United States Patent [19]

McAuslan et al.

[11] Patent Number: 5,077,215
[45] Date of Patent: Dec. 31, 1991

[54] NEUTRALIZED PERFLUORO-3,6-DIOXA-4-METHYL-7-OCTENE SULPHONYL FLUORIDE COPOLYMER SURFACE FOR ATTACHMENT AND GROWTH OF ANIMAL CELLS

[75] Inventors: Brian R. McAuslan, Clareville; John G. Steele, North Rocks; William Norris, North Sydney; Graham Johnson, Peakhurst, all of Australia

[73] Assignees: Telectronics Pty. Limited, New South Wales; Commonwealth Scientific and Industrial Research Organisation, Campbell, both of Australia

[21] Appl. No.: 360,887
[22] PCT Filed: Sep. 19, 1988
[86] PCT No.: PCT/AU88/00368
 § 371 Date: Jul. 17, 1989
 § 102(e) Date: Jul. 17, 1989
[87] PCT Pub. No.: WO89/02457
 PCT Pub. Date: Mar. 23, 1989

[30] Foreign Application Priority Data

Sep. 17, 1987 [AU] Australia ................. PI4403

[51] Int. Cl.$^5$ ............... C12N 5/00; A61F 2/02; A61F 2/04; A61F 2/06
[52] U.S. Cl. ................. 435/240.23; 424/423; 435/240.243; 623/1; 623/11; 623/12
[58] Field of Search ............ 435/240.23, 240, 243; 600/36; 623/1; 424/423

[56] References Cited

U.S. PATENT DOCUMENTS

| | | |
|---|---|---|
| 4,329,434 | 5/1982 | Kimoto . |
| 4,329,435 | 5/1982 | Kimoto . |
| 4,578,079 | 3/1986 | Ruoslahti et al. ............ 623/1 |
| 4,883,057 | 11/1989 | Broderick ............ 128/631 |

FOREIGN PATENT DOCUMENTS

| | | |
|---|---|---|
| 8665675 | 11/1975 | Australia . |
| 8671482 | 1/1983 | Australia . |
| 9184082 | 4/1983 | Australia . |
| 5014085 | 5/1986 | Australia . |
| 6048386 | 2/1987 | Australia . |
| 0092302 | 12/1983 | European Pat. Off. . |
| 2724200 | 12/1978 | Fed. Rep. of Germany . |
| 55-160029 | 12/1980 | Japan . |
| 62-288614 | 12/1987 | Japan . |
| 1311370 | 3/1973 | United Kingdom . |

OTHER PUBLICATIONS

Penner, et al., Ion Transporting Composite Membranes 1. Nafion-Impregnated Gore-Tex Journal of the Electrochemical Society, vol. 132, pp. 514–515, 1985.

Hynes Molecular Biology of Fibronectin. Annual Review of Cell Biology, vol. 1, pp. 67–90, 1985.

Adhesion of Cells to Polystyrene Surfaces, by A. S. G. Curtis et al., Departments of Cell Biology and Chemistry, University of Glasgow, Glagow G12 8QQ Scotlan, UK. the Journal of Cell Biology, vol. 97, Nov. 1983, pp. 1500–1506.

Attachment and growth of BHK cells and liver cells on polystyrene: Effect of surface groups introduced by treatment with chromic acid, H. G. Klemperer and P. Knox, Dept. of Biochemistry and Dept. of Cancer Studies, University of Birmingham Lab. Practice, vol. 26, No. 3.

Substrate Hydroxylation and Cell Adhesion, A. S. G. Curtis et al., J. Cell Sci. 86, 9–24 (1986) The Company of Biologist Ltd. Department of Cell Biology, University of Glasgow, Glasgow, UK.

(List continued on next page.)

Primary Examiner—Jacqueline Stone
Assistant Examiner—George C. Elliott
Attorney, Agent, or Firm—Oblon, Spivak, McClelland, Maier & Neustadt

[57] ABSTRACT

Neutralized surface of a polymer of perfluoro-3,6-dioxa-4-methyl-7-octene sulphonyl fluoride for attachment and growth of animal cells in vivo or in vitro, the comonomer preferably being tetrfluorethylene.

18 Claims, 10 Drawing Sheets

OTHER PUBLICATIONS

*Cellular interactions with synthetic polymer surfaces in culture* M. J. Lydon et al.,. Unilever Research Laboratory, Colworth House, Shambrook, Bedfordshire, MK44 1LQ, UK, 1985 Butterwoth & Co. (publilshers) Ltd., *Biomaterials 1985, vol. 6 Nov.*

Coating Bacteriological Dishes With Fibronectin Permits Spreading and Growth of Human Diploid Fibroblasts by Frederick Grinnell and Jannet L. Marshall, Department of Cell Biology, University of Texas Health Science Center, Cell Bio. Intern. Reports. vol. 6, No. 11, 11/82.

Adhesion and Spreading of Cells on Charged Surfaces, by N. G. Maroudas, J. Theor., Biol. (1975) 49, pp. 417–424–Imperial Cancer Research Fund Laboratories, London England.

Sulphonated Polystyrene as an Optimal Substratum for the Adhesion and Spreading of Mesenchymal Cell in Monovalent and Divalent Saline Solutions by N. G. Maroudas; –Cell Phsiol 90: 511-520, Mar., 1977.

NEUTRALIZED PERFLUORO-3,6-DIOXA-4-METHYL-7-OCTENE SULPHONYL FLUORIDE COPOLYMER SURFACE FOR ATTACHMENT AND GROWTH OF ANIMAL CELLS

FIELD OF THE INVENTION

This invention relates to the use of a copolymer of perfluoro-3,6-dioxa-4-methyl-7-octene sulphonyl fluoride and a monomer as a surface for the attachment and growth of adherent animal cells. The invention has particular application to the manufacture and use of prosthetic vascular grafts, connective tissue replacements and soft tissue replacements that incorporate such a copolymer.

BACKGROUND ART

The design or selection of materials useful in vascular prostheses requires an understanding of the characteristics necessary for irreversible endothelialisation of a surface and for inhibition of undesirable platelet interactions. An approach to the development of vascular prostheses that has been taken has been guided by the object of circumventing the acute problems of platelet activation, adhesion and thrombogenesis. This approach involves designing a blood interface which disallows thrombogenesis by preventing platelet activation directly, and may be achieved either by the selective incorporation or adsorption of platelet binding inhibitors, such as serum albumin or heparin, or by providing a surface which directly repels or inactivates platelets electrostatically. However these modifications might also suppress the attachment and growth of endothelial cells on the luminal surface of the prosthesis. Grafts prepared using this approach may therefore be regarded as unhealed and a physiological and anatomical state comparable to the normal luminal structure is not achieved.

It is generally known that surfaces which support endothelial cell growth comparable to that seen on glow discharged polystyrene also tend to be thrombogenic. However it is also known that sulphonated polystyrenes have antithrombogenic activity which is reported to be a feature of the negative charge of sulphonate groups. The present invention has been developed by following this line of investigation.

In a recent study, McAuslan and Johnson [(1987) J. Biomedical Materials Research 21.921–935] showed that the hydroxyl rich surface of poly(hydroxyl ethyl methacrylate)(pHEMA) hydrogel can be converted from a non-cell adhesive to a highly cell adhesive state by either hydrolytic surface etching or by copolymerization with methacrylic acid. Thus cell adhesion appeared to correlate with the introduction of surface COOH groups although this alone was not a sufficient condition. This has raised the question of whether other negatively charged moieties would be just as effective at promoting cell attachment.

A fluorocarbon polymer with pendant sulphonic groups is the chemically inert, non-crosslinked cation-exchange resin known by the trade mark NAFION. NAFION is chemically identified as a copolymer of tetrafluoroethylene and perfluoro-3,6-dioxa-4-methyl-7-octene sulphonyl fluoride. The mechanical and chemical stability of this perfluorosulphonate ionomer and its selective permeability to charged ions had made it useful for industrial electrochemical separating processes. It can be prepared as films or tubes and is hydrophilic, which is in contrast to polytetrafluoroethylene (PTFE, which is known by the trade mark TEFLON) or expanded PTFE (which is known by the trade mark GORE-TEX), a material which is in wide use as a vascular graft.

We have now found that any copolymer of perfluoro-3,6-dioxa-4-methyl-7-octene sulphonyl fluoride and a monomer, and particularly NAFION, may, when in a neutralised form, be used as a surface for the attachment and growth of adherent animal cells from different tissue sources, including endothelial cells. In this specification and claims, reference to being in a neutralised form means within one pH unit of pH 7.0.

DISCLOSURE OF THE INVENTION

It is an object of the present invention to provide a material useful in vascular prostheses and other implantables having improved biocompatibility arising from enhanced endothelial cell attachment properties and anti-thrombogenicity which will substantially overcome the disadvantages of the prior art.

In accordance with one aspect of the present invention, there is provided a surface for the attachment and growth of cells in vivo, said surface comprising the neutralized form of a copolymer of perfluoro-3,6-dioxa-4-methyl-7-octene sulphonyl fluoride and a monomer. Preferably, the monomer is tetrafluoroethylene. The above surface may be adsorbed or attached to an appropriate substrate that is preferably porous. The types of substrate that may be used include polymers, ceramics, metals, glass or preformed membranes. When a polymer substrate is used, the polymer is preferably porous such as polytetrafluoroethylene, expanded polytetrafluoroethylene, knitted or woven polyester and polyurethane.

In a preferred form, the surfaces of the present invention that may be used in vivo are in the form of a sponge or tube and may be adapted for use in a biosensor. The surfaces of the present invention that may be used in vivo may also be modified by selective incorporation of platelet binding inhibitors such as serum albumen or heparin or by treating the surfaces with agents that specifically repel or inactivate platelet attachment.

In accordance with another aspect of the present invention, there is provided a surface for the attachment and growth of cells in vivo, said surface comprising the neutralised form of a copolymer of perfluoro-3,6-dioxa-4-methyl-7-octene sulphonyl fluoride and a monomer optionally adsorbed or attached to an appropriate substrate as described above, and wherein said surface further includes adsorbed adhesive proteins. The preferred adhesive proteins are derived from serum and include fibronectin, vitronectin or adhesive fragments of these proteins. Other preferred adhesive proteins include laminin, collagens and thrombospondin and adhesive fragments of these proteins. The above surfaces that may be used in vivo, may also have adsorbed thereto adhesive proteins or their adhesive fragments.

In a further preferred embodiment, the above surfaces for use both in vivo and in vitro include adhered cells of the type sought to be grown.

In accordance with yet another aspect of the present invention, there is provided a process for the preparation of a surface for the attachment and growth of cells in vivo, said process comprising applying a copolymer of perfluoro-3,6-dioxa-4-methyl-7-octene sulphonyl fluoride and a monomer to an appropriate substrate. The surface so prepared must be brought to neutrality, and this may be done by either neutralizing the resultant surface or by applying the above copolymer in a neutralized form to the appropriate substrate.

The above copolymer is preferably applied to the substrate by means of radiation grafting or adhesive bonding.

In accordance with a further aspect of the present invention, there is provided a process for the preparation of a surface for the attachment and growth of cells in vitro, said process comprising exposing adhesive proteins or adhesive serum proteins to a surface comprising the neutralized form of a copolymer of perfluoro-3,6-dioxa-4-methyl-7-octene sulphonyl fluoride and a monomer optionally adsorbed or attached to an appropriate substrate, whereupon the copolymer adsorbs said proteins to form a copolymer-protein complex.

In a further preferred embodiment, the surfaces prepared according to the above processes for use both in vivo and in vitro are further exposed to cells of the type sought to be grown, whereupon the cells adhere to the said surface to further improve its cell attachment and growth properties.

In accordance with a still further aspect of the present invention, there is provided a method for the attachment and growth of cells to a surface both in vivo and in vitro, which method comprises exposing cells or a medium containing cells and adhesive proteins to a surface of the present invention.

DESCRIPTION OF PREFERRED EMBODIMENTS

Figure 1:
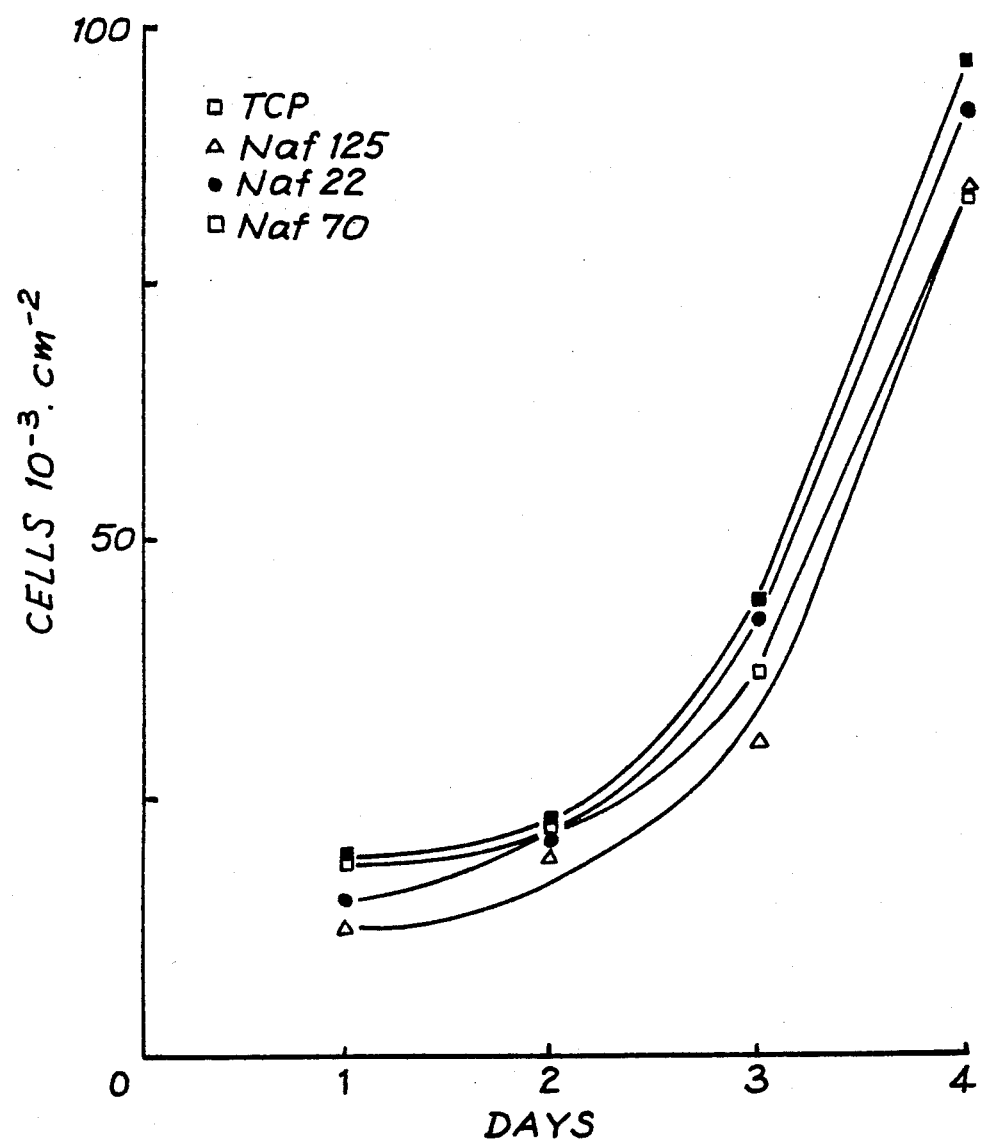
FIG. 1 is a graph of the relative growth rates of bovine aortal endothelial cells on the following surfaces: tissue culture plastic (TCP), NAFION 22, 70 and 125 films prepared as described in Example 1, during the period of 4 days after seeding, and, FIG. 2 (A and B) shows the difference in cell morphology and cell density of bovine aortal endothelial cells after 4 days culture on untreated TEFLON (FIG. 2A) or on TEFLON that was coated with NAFION, as described in Example 1, (FIG. 2B). Cells were stained with acridine orange and photographed under UV light and the photographs are at 80 times magnification.

In order that the invention may be more readily understood and put into practical effect, reference will now be made to the following examples that describe the use of NAFION as a preferred embodiment of the copolymer of perfluoro-3,6-dioxa-4-methyl-7-octene sulphonyl fluoride and a monomer.

EXAMPLE 1

Preparation of NAFION N117, NAFION N125, NAFION 22 and NAFION 70 membrane preparations, and PTFE and GORE-TEX coated with NAFION 70.

Portions of NAFION N117 membrane and NAFION N125 membrane were cut into 1 cm² pieces and washed in acetone followed by absolute ethanol. The pieces were then treated with 0.2% EDTA to remove cationic contaminants, washed thoroughly with deionised water and sterilised by autoclaving. Prior to tissue culture studies the pieces were extensively washed in sterile phosphate buffered saline (PBS) pH 7.2.

A 5% (w/vol) solution of NAFION 1100 Equivalent Weight perfluorinated ion-exchange resin was used for casting the following membranes:

i) NAFION 22—prepared by casting 0.5 ml 5% NAFION solution in the lid of a 35 mm diameter tissue culture petri dish as 22° C.

ii) NAFION 70—prepared by repeating the procedure for NAFION 22 at 70° C. for 2 hours.

Prior to tissue culture studies, the NAFION 22 and NAFION 70 membranes were sterilised under ultraviolet light for 2 hours and then extensively washed in serum free tissue culture medium.

iii) Unfilled virgin TEFLON samples were washed extensively in ethanol and some were coated with NAFION solution and some were left uncoated, for cell culture studies. Approximately 1 cm$^2$ pieces of material were coated with 50 microliters of 5% NAFION Equivalent Weight 1100 solution and treated at 70° C. for 2 hours. Substrates so prepared and tissue culture polystyrene (TCP) were sterilised under UV light for 2 hours and washed extensively in serum free tissue culture medium before being used for cell culture studies.

Equilibrium water content (EWC)

The EWC of both NAFION N125 and the NAFION 22 and 70 membranes was determined essentially as described by Pedley and Tighe ](1979) Br. Polym. J., 11, 130–135]. In both cases the NAFION was pretreated with 0.2% EDTA and then washed and equilibrated in deionised water for 4 to 6 days before weighing.

Results

Commercially available preformed sheet NAFION (NAFION N-117 and N-125) and NAFION membrane cast from a 5% solution on either glow discharged or non-glow discharged polystyrene at 22° C. (NAFION 22) were transparent neutral coloured substrates. After casting at 70° C. (NAFION 70), no difference in texture of colour was observed. However this treatment rendered it insoluble in ethanol and acetone. NAFION membranes were cast in a variety of thickness from approximately 10 to 40 microns. By comparison the preformed sheet NAFION used in this study was approximately 100 microns thick. NAFION N125 has an equilibrium water content of 12.0% and NAFION 22 and 70 equilibrium water contents of 32% and 36% respectively. NAFION membranes cast on polystyrene could be peeled off the surface by gently pulling with forceps and the thickness of the membrane determined the fragility of such material.

EXAMPLE 2

Attachment and Growth of Bovine Endothelial Cells and other Adherent Animal Cells on NAFION

Methods

Cell Culture and Cell Growth Rate Determination

A clonal line of normal bovine aortic endothelial (BAE) cells were grown and maintained in M199 cell culture medium supplemented with 20% (v/v) fetal calf serum. To determine the increase in the number of cells growth on the different substrates, 2 ml of M199 cell culture medium supplemented with 20% foetal bovine serum containing between $5 \times 10^4$ and $2 \times 10^5$ BAE cells were added to dishes containing NAFION N125, or coated with either NAFION 22 or NAFION 70, and incubated in a humidified atmosphere of 5% $CO_2$ in air at 37° C. After 6 hours, cell attachment was estimated by counting cells within 15 randomly chosen 0.931 mm$^2$ areas. Each polymer sample was the subject of three individual trials and mean cell numbers expressed per cm$^2$. After this initial period cell numbers were determined every 24 hours to determine cell growth rate. For comparison the growth of BAE cells on GORE-TEX, TEFLON and glow discharged tissue culture polystyrene was also determined. Cell morphology was investigated by routine light microscopy of cultured surfaces for the NAFION membranes. For the NAFION cast onto TEFLON surfaces, the opacity of the TEFLON precluded the use of phase contrast microscopy for a full visual comparison, so cells were fixed with 2.5% gluteraldehyde, stained with 3 mM acridine orange then photographed under UV light.

Results

It is known that NAFION is a strong acid and washing the cast polymers (NAFION 22 and NAFION 70) in serum-free tissue culture medium showed that a comparatively large volume of medium was required to neutralise its acidic property. This is therefore, an important aspect of the use of NAFION as a substrate for cell growth which must be taken into account in its preparation. Similarly, NAFION preformed membrane (NAFION N117 and NAFION N125) required neutralisation before use for cell culture.

A wide range of different cell types have been successfully grown on NAFION. These include bovine aortic endothelial cells (BAE), bovine aortic smooth muscle cells, bovine corneal endothelial cells, bovine retinal capillary endothelial cells, baby hamster kidney fibroblasts, and 3T3 fibroblasts. All cell types displayed their own characteristic morphology and growth characteristics when observed on TCP control dishes. Endothelial cells formed a cobblestone pavement monolayer whilst fibroblasts showed spindle shaped morphology and eventually formed a whorl-like pattern.

Figure 2A:
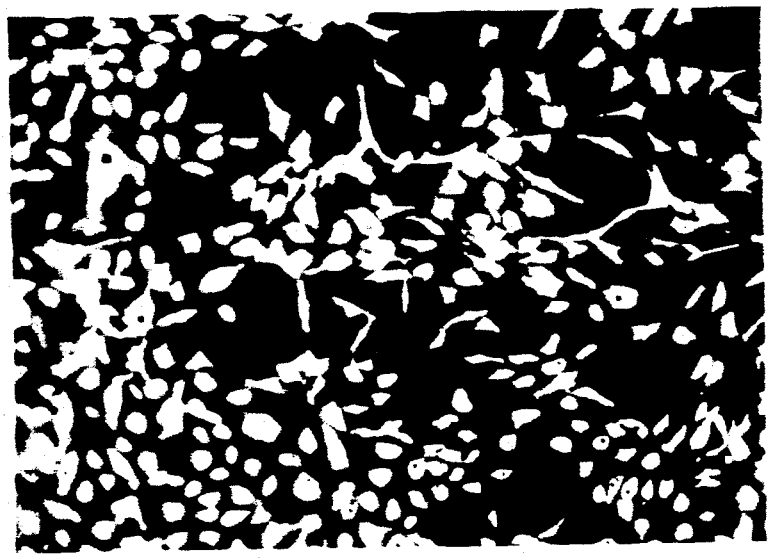
Figure 2B:
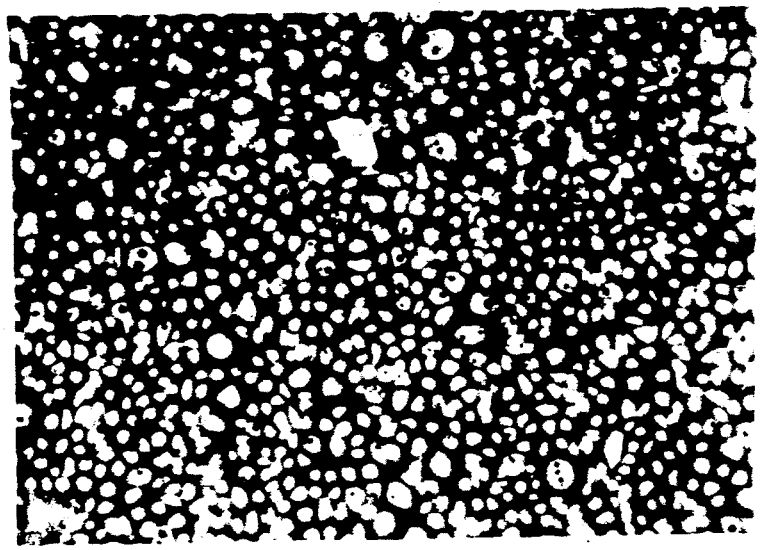

Since it was proposed that the material might show potential as a component of a vascular prosthesis the attachment and growth of BAE cells on NAFION compared to TCP and TEFLON was studied in some detail. Cell attachment in vitro was found to be dependent on the presence of serum; and in the absence of serum no cells were attached to any of the NAFION preparations after six hours. The attachment of BAE cells to the different substrates after 6 hours was expressed with respect to cell attachment to tissue culture polystyrene (which was set as 100%). The BAE cell attachment to NAFION 70 and NAFION 22 was 109±3.2% (Mean Standard Deviation) and 97±3.6% respectively; to NAFION N125, 84±3.2% and to TEFLON, 75±6.8%. Of particular interest is the fact that cells appeared to be more evenly distributed on the surface of the NAFION films that on NAFION N-125 or tissue culture polystyrene. FIG. 1 shows the kinetics of growth of BAE cells on NAFION N-125, 22 and 70 compared to their growth on tissue culture polystyrene after 4 days. Only small differences were seen in the growth rates and final numbers of cells on the NAFION preparations compared with TCP. The growth rate of BAE cells on NAFION preparations observed in these experiments was considerably higher than the level recognised for such cells on the commonly used TEFLON vascular graft material. Cell growth on NAFION coated TEFLON showed a similar improvement, over such cells grown on TEFLON alone. By casual appraisal cells cultured on TEFLON had a slower growth rate than cells cultured on the other polymers. In contrast to BAE cells seeded on NAFION, cells seeded on TEFLON failed to achieve the characteristic polyhedral morphology and remained fibroblastoid until almost confluent. This effect was demonstrated by growing $10^5$ BAE cells/ml in culture for 4 days on untreated TEFLON and NAFION coated TEFLON. BAE cells grown on untreated TEFLON displayed a typical patchiness or fibroblast-like morphology in the areas of sparse cover (FIG. 2a). This is characteristic of BAE cells when growing on a less than ideal substrate. In contrast, BAE cells grown on NAFION coated TEFLON achieved the polyhedral morphology characteristic of such cells grown on ideal substrates (FIG. 2b). Further, BAE cells could be maintained in culture on NAFION N125 successfully for up to 3 weeks.

The growth of BHK fibroblasts on non-glow discharged polystyrene was facilitated by coating the surface with NAFION solution. In accordance with the findings for BAE cells, no difference between the behaviour of BHK fibroblasts to NAFION 22 compared to glow discharged polystyrene was seen whereas cells failed to attach and spread properly or nonglow discharged polystyrene (results not shown). Attachment of BAE cells to TEFLON was less strong than to polystyrene or NAFION as seen when only gently pipetting of medium or PBS with a Pasteur pipette was sufficient to detach the cells from the TEFLON surface. Such physically weak attachment to tissue culture polystyrene and NAFION was not seen.

EXAMPLE 3

Attachment and Growth of Human Endothelial Cells and other Human Cells on NAFION 70 Membrane Preparations.

Methods

In some experiments of this Example, the serum adhesive glycoprotein fibronectin (Fn) was removed from serum prior to use of the serum for cell culture by passage over a gelatin-Sepharose affinity column. Serum treated on a gelatin-Sepharose column was confirmed to be free of Fn by immunoassay of the Fn content. In other experiments, the serum adhesive glycoprotein vitronectin (Vn) was removed by passage over an affinity column consisting of immobilized anti-Vn antibody. The sera that were depleted in Vn by this affinity technique were confirmed to have been exhaustively stripped of vitronectin by immunoassay for Vn content.

Human cell lines HeLa from cervical carcinoma, HeP-2 from carcinoma of Larynx, and HT 1080 from human fibrosarcoma were grown in a growth medium consisting of minimal essential medium supplemented with 10% (v/v) foetal calf serum, 60 microgram/ml penicillin and 100 microgram/ml streptomycin.

A human umbilical artery endothelial (HUAE) cell culture was established and grown in 75 cm$^2$ tissue culture polystyrene (TCP) flasks coated with Fn. Coating with Fn was achieved by incubating the flasks with 5 ml solution of 40 ug/ml Fn in PBS at 37° C. for 1 hour prior to cell seeding. Excess solution was removed before cells were added. The cells were routinely maintained in a growth medium consisting of an equal mixture of McCoy 5A (modified) and BM86-Wissler media supplemented with 30% v/v foetal bovine serum, 40 ng/ml fibroblast growth factor, 60 ug/ml endothelial cell growth supplement, 20 ug/ml insulin, 60 ug/ml penicillin and 100 ug/ml streptomycin. The cells were routinely passaged using trypsin-versene, and for experimental work cells were used between passage 15 and passage 20 (inclusive).

For attachment and cell growth studies, NAFION 70 films cast onto 22 ml wells were equilibrated with PBS, and 2 ml of growth medium containing $5 \times 10^4$ cells was added to each well. The cell attachment was determined by counting, in randomly selected field, the total number of cells and the number of these cells that had spread onto the surface. Cell growth in each well was quantitated by counting 5 randomly selected fields per well after successive days of culture, until cell confluence was reached. The mean and standard error of cell number per cm$^2$ for triplicate samples were determined.

GORE-TEX samples were cut into pieces of approximately 1 cm$^2$, coated with approximately 0.3 ml NAFION solution per piece, then immediately treated at 70° C. for 2 hrs. The NAFION-coated GORE-TEX was exposed to UV light for 2 hrs and then washed extensively in serum-free tissue culture medium. Some samples were then coated with 40 ug/ml Fibronectin for 45–60 min at 37° C. prior to seeding with HUAE cells.

Results

Figure 3A:
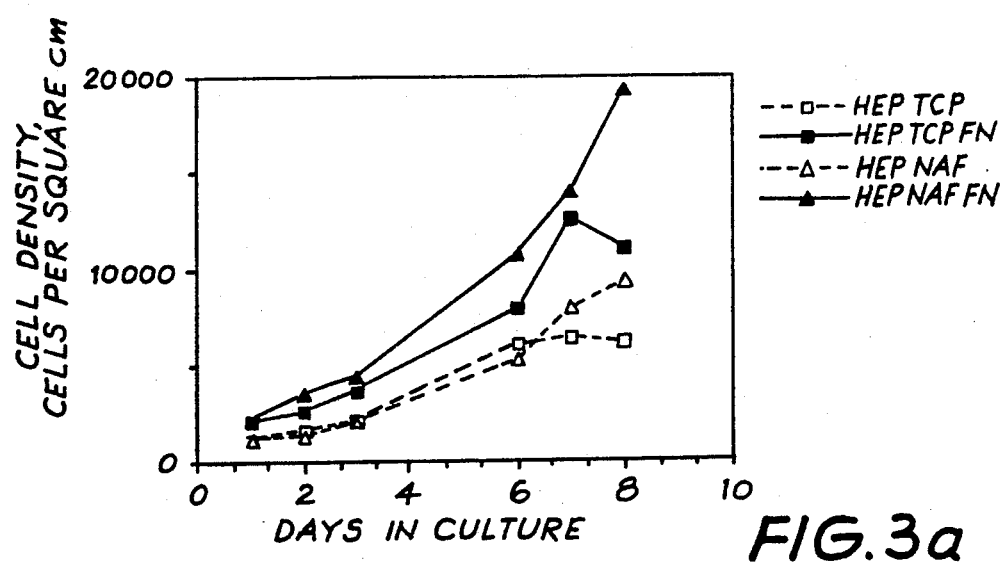
FIG. 3a is a graph of the relative growth rate of the human cell line Hep-2 on the following surfaces: tissue culture plastic, NAFION 70 prepared as described in Examples 1 and 3 and both the above surfaces precoated with fibronectin prior to cell seeding, cultured for a period of 7 days.
Figure 3B:
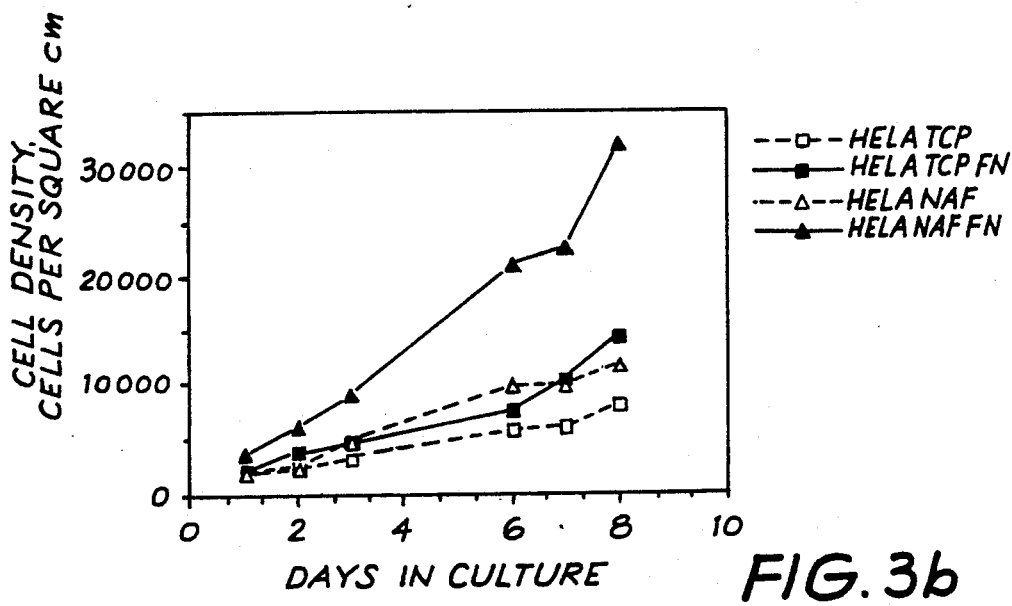
FIG. 3b is a graph of the relative growth rate of the human cell line HeLa on the following surfaces: tissue culture plastic, NAFION 70 prepared as described in Examples 1 and 3 and both the above surfaces precoated with fibronectin prior to cell seeding, cultured for a period of 8 days.
Figure 3C:
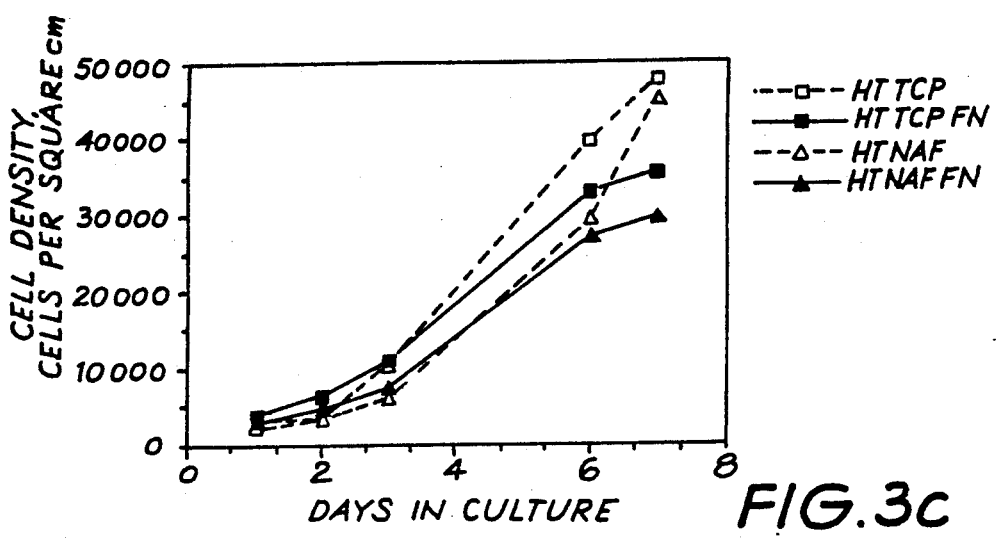
FIG. 3c is a graph of the relative growth rate of the human cell line HT 1080 on the following surfaces: tissue culture plastic, NAFION 70 prepared as described in Examples 1 and 3 and both the above surfaces precoated with fibronectin prior to cell seeding, cultured for a period of 7 days.
Figure 4A:
FIG. 4 (A-D) shows the difference in morphology of human umbilical arterial endothelial cells cultured on tissue culture plastic (FIG. 4A and FIG. 4C) or NAFION 70, prepared as described in Examples 1 and 3 (FIG. 4B and FIG. 4D). Some of the surfaces (FIG. 4C and FIG. 4D) were precoated with fibronectin prior to cell seeding. The cells were cultured for 7 days then photographed. The photographs in FIG. 4A and FIG. 4B are at 110 times magnification and in FIG. 4C and FIG. 4D, at 220 times magnification. Note that the morphology of the cells on NAFION 70 is indistinguishable from that of the cells on the tissue culture plastic, and not also the enhanced cell spreading on each of the surfaces when precoated with fibronectin.
Figure 4B:
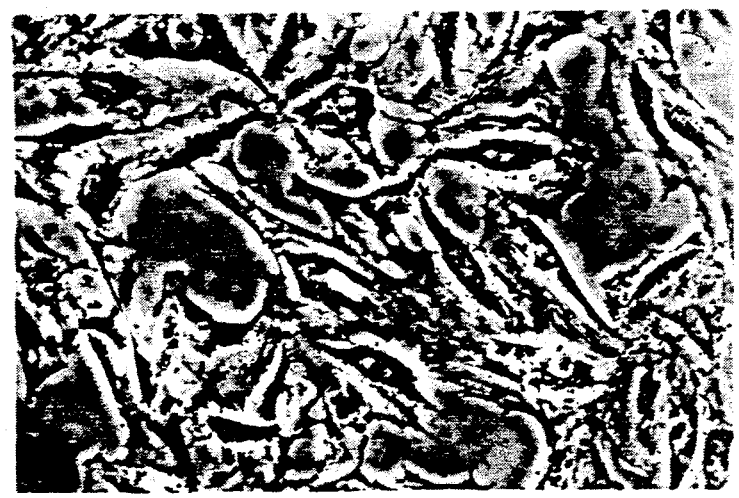
Figure 4C:
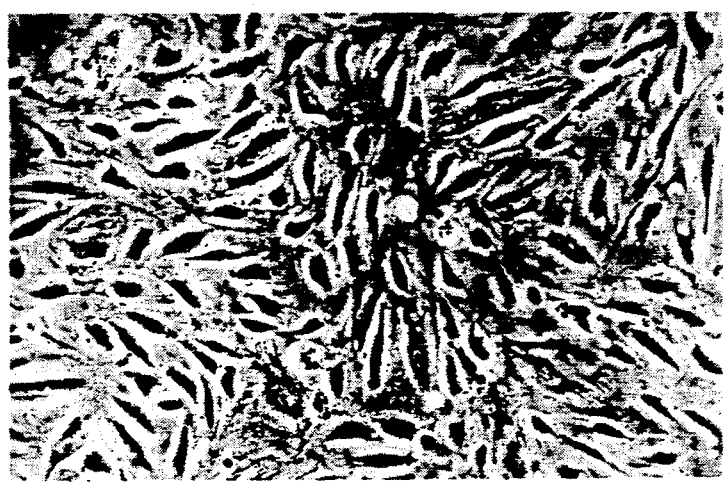
Figure 4D:
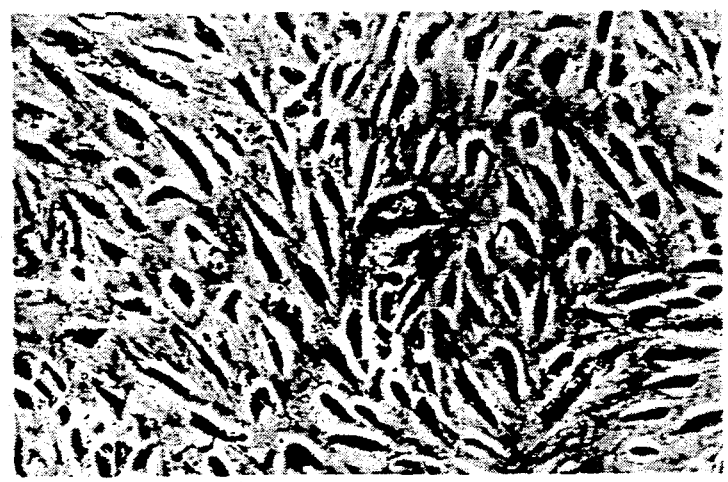

The attachment and growth of human cell lines Hep-2, HeLa and HT 1080 was compared to that on tissue culture polystyrene (TCP). Cell attachment and growth was also determined on NAFION films that had been coated with a solution of 40 ug/ml Fibronectin. The human cell lines Hep-2, HeLa and HT 1080 all attached and grew on NAFION films (see FIG. 3 for cell growth curves). It was necessary to use culture medium that contained serum for the cells to attach and to grow on the NAFION surface. In the case of cell lines Hep-2 and HeLa, the rate of cell growth was increased where the NAFION film had been precoated with Fn (see FIG. 3 for comparison of Fn coated NAFION and NAFION that had not been coated with Fn) whereas in the case of HT 1080 cells the Fn coating of the NAFION had no positive effect on the cell growth rate.

HUAE cells were grown on NAFION and compared to growth on TCP. It was also necessary to use culture medium that contained serum for the HUAE cells to become attached and to grow. Fn-coated TCP was also included as a control surface, as this surface is known to support good HUAE cell attachment and growth. The number of HUAE cells attached to the NAFION surface as viewed after 4 hours fo cell seeding was equivalent to that on TCP, whereas for the Fn-coated NAFION, the number of cells attached was equivalent to that on the Fn-coated TCP. The morphology of the HUAE cells attached to the NAFION surface was generally similar to that of the HUAE cells seeded onto TCP, see FIG. 4. This morphology indicated that although the HUAE cells had attached to the NAFION surface when seeded in the presence of serum, the cells had not formed the well spread morphology that is typical of HUAE cells that have been seeded onto Fn-coated TCP. However the morphology of the HUAE cells that attached to the Fn-coated NAFION films was well spread and the cell morphology was similar to HUAE cells growing of Fn-coated TCP, see FIG. 4.

Figure 5A:
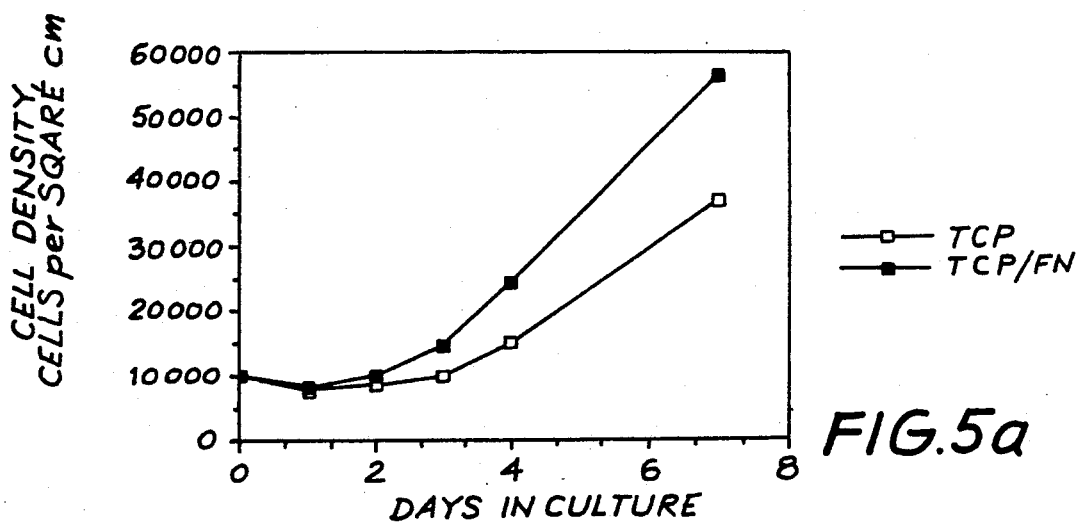
FIG. 5a is a graph of the relative growth rates of the human umbilical arterial endothelial cells cultured for 7 days on tissue culture plastic (TCP) and TCP precoated with fibronectin prior to cell seeding.
Figure 5B:
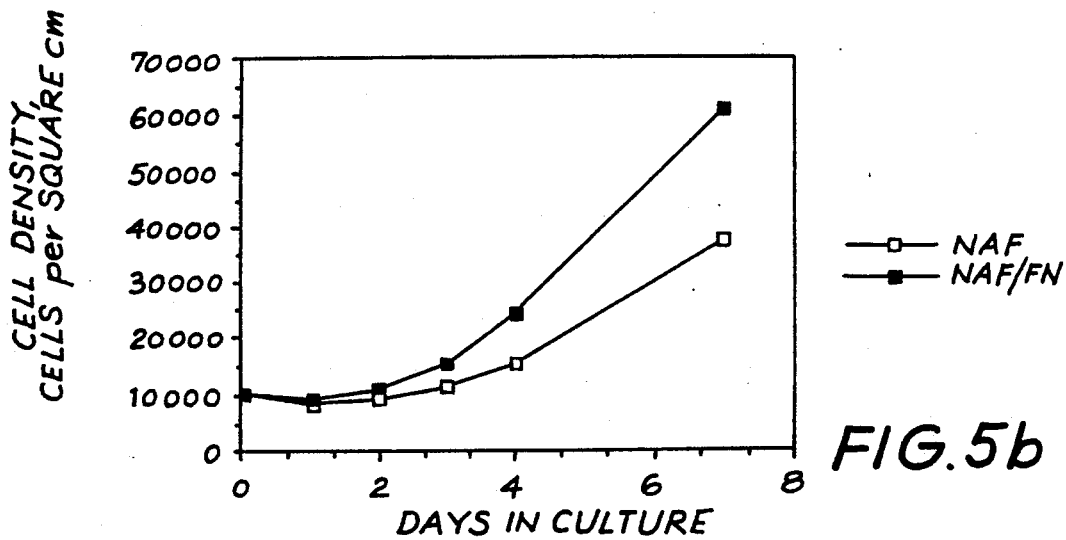
FIG. 5b is a graph of the relative growth rates of the human umbilical arterial endothelial cells cultured for 7 days on TEFLON that was coated with NAFION (NAF) as described in Example 1, and NAF precoated with fibronectin prior to cell seeding.
Figure 5C:
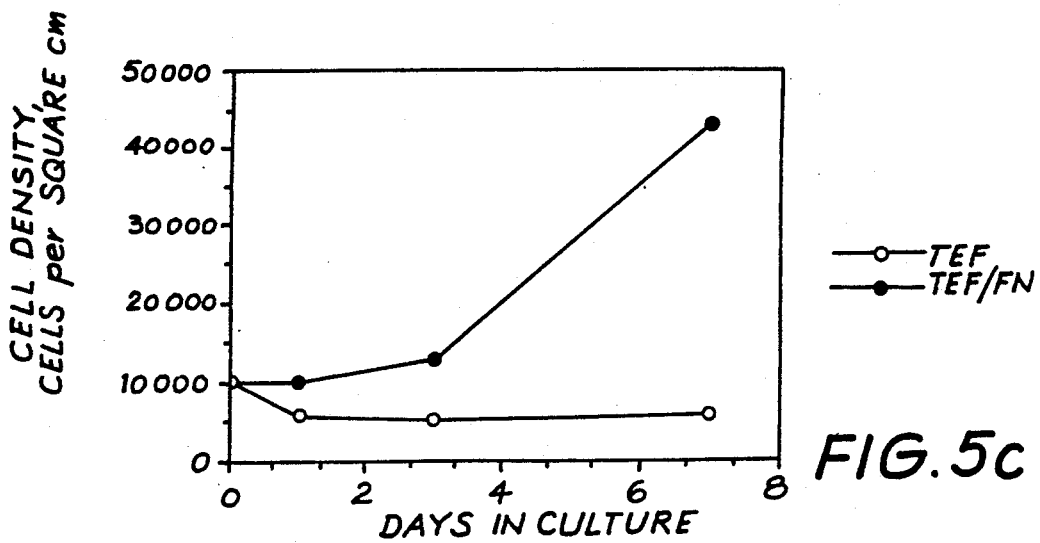
FIG. 5c is a graph of the relative growth rates of the human umbilical arterial endothelial cells cultured for 7 days on untreated TEFLON (TEF), and TEF precoated with fibronectin prior to cell seeding.
Figure 6A:
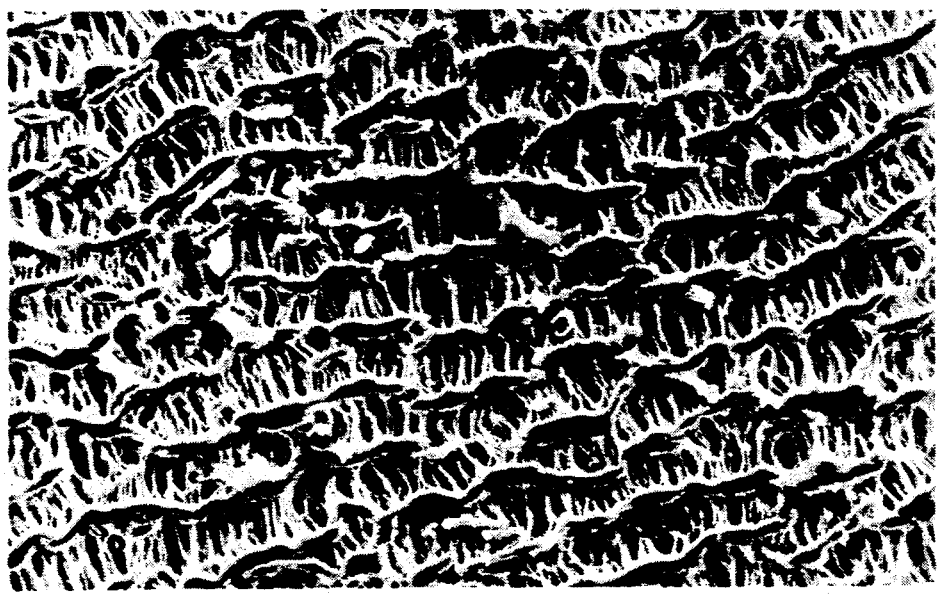
FIG. 6 (A-F) shows the difference in morphology of human umbilical arterial endothelial cells cultured on GORE-TEX (FIG. 6A and FIG. 6B), or GORE-TEX that was coated with NAFION as described in Example 3 (FIG. 6C and FIG. 6D). Another sample of NAFION-coated GORE-TEX (FIG. 6E and FIG. 6F) was precoated with fibronectin prior to cell seeding. The cell attachment and morphology was examined by scanning electron microscopy and the magnification of each panel is given as follows: for FIG. 6A, FIG. 6C and FIG. 6E, 200 microns=62 mm on the print, whereas for FIG. 6B, FIG. 6D and FIG. 6F, 50 microns=61 mm on the print. Note the sparce cell attachment to GORE-TEX (FIG. 6A and FIG. 6B) but markedly better cell coverage and spreading on the GORE-TEX that was coated with NAFION, giving almost complete cell coverage of the surface (FIG. 6C to FIG. 6F). The cells were fixed after 1 day of culture (FIGS. 6A, 6B, 6C, 6D, 6F) or 3 days of culture (FIG. 6E).
Figure 6B:
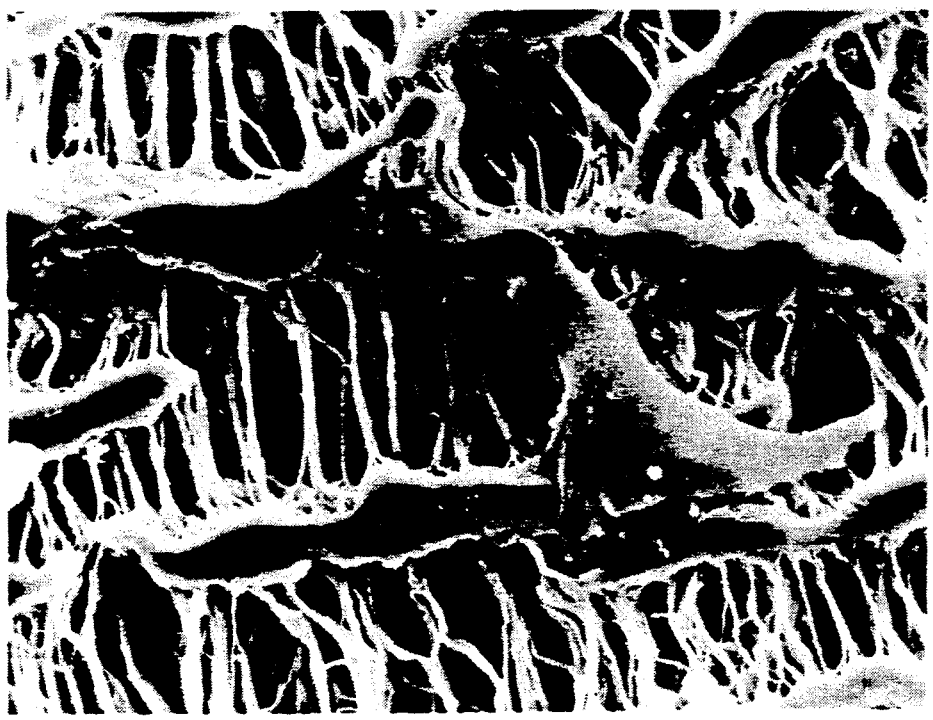
Figure 6C:
Figure 6D:
Figure 6E:
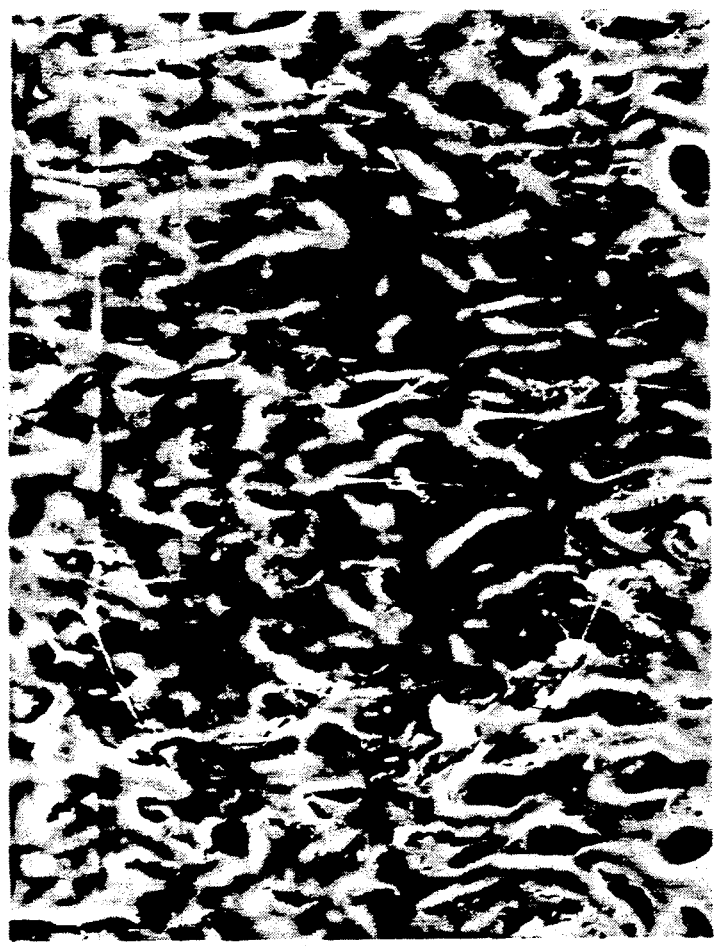
Figure 6F:

HUAE cells grew on the NAFION and Fn-coated NAFION surfaces at a rate that was similar to the cell growth on TCP and Fn-coated TCP, respectively (see FIG. 5 for growth curve).

The role that Fn from the serum and Vitronectin from the serum may play in the attachment of the HUAE cells to the NAFION and Fn-coated NAFION surfaces was determined by selective removal of these components from the serum used in the culture medium in which the cells were seeded. Selective removal of Vn from the culture medium completely abolished the attachment of HUAE cells to the NAFION surface. The importance of Vitronectin (which is also known as serum spreading factor, epibolin or 70K spreading factor) has been previously reported for other polymer surfaces such as tissue culture polystyrene, see Grinnell [(1976) Exp. Cell Res., 97, 265–274 and (1977) Exp. Cell Res., 110, 175–190]. Attachment of HUAE cells to Fn-coated NAFION over a 4 hour period when seeded in culture medium containing Vn-depleted serum was equivalent to that of HUAE cells seeded in intact medium onto the Fn-coated surface.

The selective removal of Fn from the seeding culture medium did not abolish the attachment of HUAE cells to the NAFION surface. As a consequence of removal of serum Fn, the rate of cell attachment was somewhat reduced over the first 4 hours as compared to cell attachment to NAFION where the culture medium contained intact serum. However after 24 hours the HUAE cell coverage of the NAFION surface with the Fn-depleted culture medium was identical to that seen on the NAFION surface with the medium containing intact serum. The use of culture medium containing vitronectin-depleted serum for seeding of HUAE cells onto Fn-coated NAFION surface did not effect the rate and extent of HUAE cell attachment and cell morphology, as compared to that where the HUAE cells were seeded onto Fn-coated NAFION using culture medium containing intact serum.

These results indicate that the serum-dependence of the attachment, cell spreading and growth of HUAE cells on a NAFION surface that has not been precoated with purified Fn or other adhesive proteins involves as an essential component the serum adhesive glycoprotein Vitronectin. Vitronectin from serum or culture medium containing serum is known from previous work to adsorb readily onto other culture surfaces such as tissue culture polystyrene. The results also indicate that the NAFION surface is similar to other surfaces used for the attachment of cells in that the adhesive glycoprotein Fn may be purified from serum and then coated onto the NAFION surface to give a substratum that supports good HUAE cell attachment, with consequential effects on cell growth. Taken together, these results indicate that the adsorption of adhesive serum proteins such as vitronectin or fibronectin onto a NAFION surface produces a substratum for promoting cell adhesion and growth.

GORE-TEX-NAFION-Fn as a substratum for HUAE cell growth

NAFION was coated onto GORE-TEX, then the NAFION GORE-TEX surface was seeded with HUAE cells. In some samples the NAFION-GORE-TEX surface was precoated with Fibronectin prior to cell seeding. The HUAE cells attached to the NAFION-GORE-TEX surface and grew to produce a surface that was almost completely covered with HUAE cells (See FIG. 6). The HUAE cells grown on each of the NAFION-GORE-TEX surface and the fibronectin-coated nation-GORE-TEX surface had a well attached and spread morphology as observed in the scanning electron microscope (see FIG. 6).

EXAMPLE 4

Attachment and Growth of Ovine Endothelial Cells on NAFION tubes.

Methods

Figure 7:
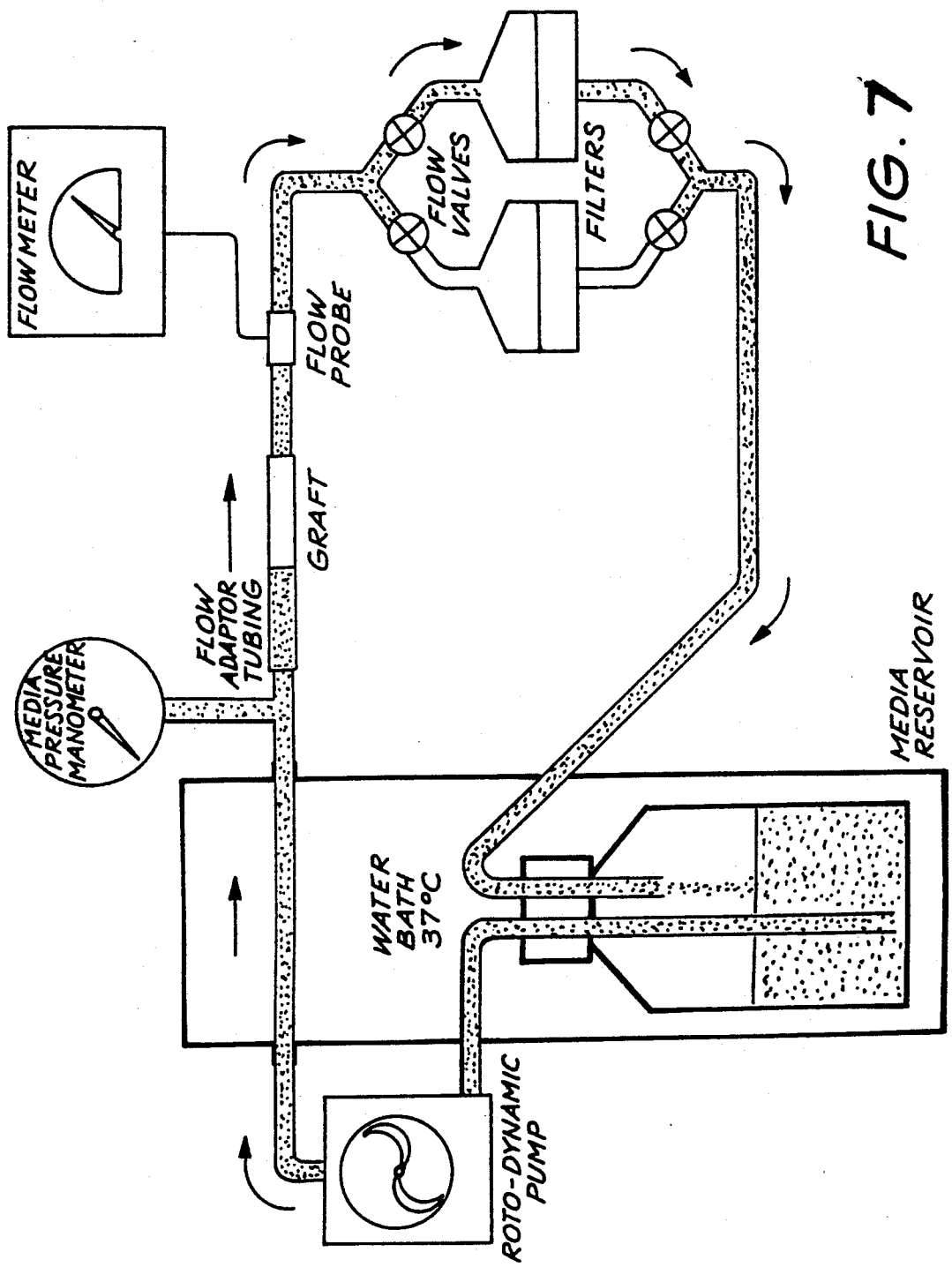
FIG. 7 is a diagram of the apparatus used to test cellular attachment under conditions of flowing culture medium, as described in Example 4.

An ovine carotid arterial endothelial (OCAE) cell culture was established after the methodology of Jaffe ((ed) Biology of Endothelial Cells (Developments in Cardiovascular Medicine) 1984, Martinus Nijhoff Publishers, Boston), and routinely maintained in McCoy 5A (modified) medium supplemented with 20% foetal bovine serum, 60 ug/ml penicillin and 100 ug/ml streptomycin and passaged using trypsin-versene. For experimental work, cells were used between passage 6 and passage 12 (inclusive). Preequilibrated NAFION tubes (2.9 mm internal diameter and 25 mm in length) were incubated with a 40 ug/ml solution of fibronectin (Fn), washed with PBS and individually placed into sterile-cap polystyrene vials, then 9 ml of growth medium containing $2 \times 10^6$ cells was added to each via. The cell suspension was gassed with a mixture of 5% $CO_2$ in air and the vial tightly sealed. The vials were then placed inside a TCP roller bottle and firmly held in a position by packing. The loaded bottle was then rotated at 1 r.p.m. on a roller at 37° C. The culture medium was replenished at 24 hr and 72 hr and the tubes removed for subsequent flow testing after 5 days. Cell growth could be observed through the NAFION tube using a phase contrast microscope. Having observed that the tubes support cell attachment and growth over 5 days, the tubes were cultured for 6 hr in culture medium consisting of Dulbecco's modified Eagle's medium containing glutamine, 3 mg/l methionine and 25 uCi/ml of 35S-methionine, then further incubated with the normal (McCoy 5A medium with serum and supplements) medium for a further 15h. The tubes containing the metabolically-labelled cells were briefly washed in PBS then inserted into the flow test system as detailed in FIG. 7. The tubes were subjected to increasing flow rates of a medium consisting of McCoys 5A medium containing 20 mM Hepes buffer (pH 7.2) and 20% (v/v) foetal bovine serum at 37° C. for the specified time periods. Cells released from the tubes were collected on the downstream glass fibre filters and quantitated by radioactive determination (liquid scintillation counting). Following the flow studies, the tube was removed and bisected then half of the tube was examined for adherent cells by microscopic techniques and the cells on the other half were removed using trypsin-versene and the radioactivity in the released cells was determined Results In view of the results with HUAE cells where enhanced cell spreading, attachment and growth was produced by precoating the NAFION surface with Fibronectin (Example 3 above), the NAFION tubes that were used in the flow experiments were precoated with Fn. OCAE cells seeded into the Fn-coated NAFION tubes attached to the luminal surface and formed a confluent monolayer of cells during 3 to 5 days of culture. The cells attached to the tube were tested for cellular attachment in an in vitro flow system that permitted laminar flow (at flow rates up to 207 ml/min, equivalent to 12.6 dynes/cm$^2$ shear force, and above this flow rate, turbulent flow, see FIG. 7 for design). The OCEA cells withstood the shear force treatments of up to 20 dynes/cm$^2$, with negligible cell detachment during the flow treatment (see Table 1 below). The cellular monolayer was examined microscopically after the flow treatment and the cells remained attached and well spread to the luminal surface of the tube, with no evidence of detachment or damage to the cells. These experiments show that the endothelial cells form strong attachment to the Fn-coated NAFION tube surface and can withstand shear forces that are equivalent to those that would be encountered in vivo.

TABLE 1

Retention of OCAE cells on NAFION tubes under fluid flow conditions

| Experiment | % cells remaining attached to tube | % cells detached and recovered on filters |
| --- | --- | --- |
| 1 | 99.4 | 0.6 |
| 2 | 99.1 | 0.9 |
| 3 | 99.0 | 1.0 |
| 4 | 98.2 | 1.8 |
| 5 | 97.8 | 2.2 |

The cells were cultured on Fibronectin-coated NAFION tubes as described in the text above, then the cells attached to the tubes were subjected to the following flow protocol: 10 min at a flowrate of 66 ml/min corresponding to a shear force of 4 dynes/cm$^2$ followed by 10 min at 132 ml/min equivalent to 8 dynes/cm$^2$, then 10 min at 198 ml/min equivalent to 12 dynes/cm$^2$, then 10 min at 264 ml/min equivalent to 16 dynes/cm$^2$, then 10 min at 330 ml/min equivalent to 20 dynes/cm$^2$. It should be noted that the increase in flow corresponding to the step going from 12 to 16 dynes/cm$^2$ necessitated going from laminar to turbulent flow.

EXAMPLE 5

Studies of in vitro thrombogenicity of NAFION surfaces.

In vitro thrombogenesis of TEFLON, NAFION, tissue culture polystyrene and vitrogen coated polystyrene surfaces, were studied in the following manner:

(i) Human Platelet Binding

Human platelets prepared from fresh human plasma were labelled with Chromium 51. Platelets collected by centrifugation were labelled with Cr-51 in 0.25 M HEPES/tris buffer pH 7.0 containing a stock solution of Cr-51 in 0.2 HEPES/tris buffer for 1 hr at room temperature. The percentage incorporation of Cr-51 into platelets was checked by counting the amount of radioactivity incorporated in platelets collected by centrifugation and unincorporated radioactivity in the supernatent. Incorporation of the label was then inhibited by the addition of 5% ascorbic acid. Platelets were incubated in the presence of the polymer surface under study in a 96 well ELISA tray for 3 hours at room temperature. The polymers were the removed and washed thoroughly in 0.14M NaCl/0.02 HEPES buffer pH 7.0 and bound radioactivity determined by counting the polymers in a gamma counter. Results were expressed as numbers of platelets bound to the polymer surface per mm$^2$.

(ii) Partial thromboplastin time

Partial thromboplastin time was determined by incubating platelet poor plasma (Prepared by centrifugation) in the polymer surface in glass tubes. 0.1M NaCl was added to the plasma and the time for clot formation measured. This time was taken as the partial thromboplastin time.

Results

The platelet binding experiments showed that polystyrene, TEFLON and NAFION bound between approximately 12,000 and 18,000 platelets per mm$^2$ whereas polystyrene coated with vitrogen 100 (purified collagen) bound 163,682 platelets per mm$^2$. Actual figures obtained were for polystyrene 15,023; for TEFLON 17,860 and for NAFION 18,070 platelets per mm$^2$. Partial thromboplastin times revealed that NAFION required 210 seconds for clot formation followed by vitrogen 100-coated polystyrene that required 238s; TEFLON 247 s and polystyrene 250 s.

These data indicate that NAFION and TEFLON have similar partial thromboplastin times and platelet binding properties (low, compared to collagen surfaces) which suggests that NAFION is no more thrombogenic than TEFLON.

EXAMPLE 6

Porous NAFION Implants

The use of autograft material is still the most desirable method used to replace diseased or damaged tissues or organs. However, due to anatomical or other considerations, such as those of infection or rejection, this approach may not be feasible. Of particular challenge is the repair of connective tissue defects. Both naturally derived and synthetic materials have been used in this regard, for example, injectable solubilized collagen and polymeric hydrogels. There is increasing interest in the provision of synthetic materials as components of prosthetic devices.

Methods

NAFION implants were prepared by mixing a 5% solution of NAFION Equivalent Weight 1100 with NaCl crystals in approximately 10:1 ratio. The mixture was poured into either glass petri dishes or small (20 ml) volume beakers and incubated at 60° C. for between four and seven days. After this time the NaCl was dissolved in distilled water. However, implants could have been made by alternative techniques described in the art, e.g. sintering, thermal expansion, laser or ion beam drilling, etc. The material samples were sterilized prior to implantation using an industrial method of ethylene oxide processing. In vivo biocompatibility testing was conducted using males of an inbred strain of BALB/c mice. Animals were anaesthetised using ether and their dorsal and flank regions prepared by clipping the fur and swabbing with HIBITANE disinfectant (10% in 70% ethanol, each (v/v)). Implants were inserted subdermally by making a small incision with a pair of scissors and further blunt dissection to prepare a small pocket into which each implant was placed. The skin was closed using two sutures (Mersilk 4.0) and swabbed again with HIBITANE. Each animal received one implant of the material and was caged separately after surgery. Animals were biopsied after one, three, four, six and twelve weeks. At biopsy, implants were examined macroscopically for signs of lysis or gross inflammation, excised with the overlying skin and fixed in 10% formaldehyde in normal saline. The tissue was dehydrated in ethanol and prepared for routine histology by embedding in Historesin (LKB); 2 mm sections were stained with haematoxylin and eosin and viewed in an Olympus BH-2 microscope.

Results

All implants were recovered progressively up to 12 weeks. Macroscopic examination revealed that no overt tissue inflammation was present. An indication of the resistance of the implant to cellular degradation was that the original angular contours of the cut edges of the implants were still visible even after 12 weeks in vivo. Implants appeared to maintain their original size throughout the 12-week study period. Histological examination showed that after one week, implants were infiltrated with lymphocytes and a highly cellular connective tissue capsule had formed around the periphery. Lymphocytes had also migrated into the centre of the implants. Three and four week implants appeared similar. Peripheral aspects of the implants were well embedded in the fibrous tissue surrounding the implant. Some fibrous tissue ingrowth was seen particularly after four weeks, as was the presence of large capillaries. At this stage multinuclear giant cells were seen in close association with the implants. After six weeks cellular and fibrous tissue ingrowth was well developed. The lymphocyte inflammatory response was reduced by this time however more multinuclear giant cells were found around the edges of the implants. Twelve weeks after implantation, isolated fingers of fibrous tissue had extended into the centre of most of the implants. These were populated by fibroblasts and lymphocytes and contained small blood capillaries. All implants were well embedded in host tissue and larger blood vessels were observed growing across the surface of the implants. The implants showed no sign of material degradation.

In summary Examples 1 to 5 demonstrate the excellent cell response to NAFION in different forms. By successfully growing a number of mammalian cell types, notably human arterial endothelial cells, on a variety of NAFION substrates we have shown that NAFION has good cell supportive characteristics. In particular, we have demonstrated the efficacy of NAFION coated TEFLON for support of endothelial cell growth, and that endothelial cells grown on NAFION tubes by the procedures contained in this invention resist shear forces due to fluid flow. It is generally understood that a covering of only approximately 20% of the luminal surface of a vascular graft by metabolising endothelial cells is required to avoid thrombogenesis and we have shown that a morphologically normal endothelial surface is achieved quickly on NAFION. This is in contrast to attempts to culture endothelial cells on TEFLON where cells remain fibroblastoid until reaching confluence and are poorly attached to the surface. Example 6 demonstrates the biological acceptance of porous NAFION implants indicating that NAFION may be useful for connective tissue or soft tissue prostheses.

These results suggest that NAFION or indeed any copolymer of perfluoro-3,6-dioxa-4-methyl-7-octene sulphonyl fluoride and a monomer, may be used for the in vitro attachment and growth of animal cells, and may be incorporated into a vascular prosthesis or be a useful alternative to commercially available materials currently used as components of vascular prostheses. Preferably, the copolymer of the present invention may be readily cast into tubes or coated onto pre-existing tubes to serve as an effective vascular graft. The effectiveness of the said copolymer as a component of a vascular graft may be further enhanced by the many apparent variations in its preparation as discussed with reference to NAFION herein. The use of the said copolymer as a surface for endothelial cell attachment and growth may be of particular value in the new technique of cell seeding of vascular grafts and prostheses prior to implantation.

The foregoing describes only some embodiments of the present invention and modifications obvious to those skilled in the art, can be made thereto without departing from the scope and ambit of the invention.

We claim:

1. In a prosthesis or sponge implantable in a body, the improvement comprising forming the surface of said prosthesis or sponge from a neutralized copolymer of perfluoro-3,6-dioxa-4-methyl-7-octene sulphonyl fluoride and a monomer.

2. The prosthesis or sponge of claim 1 wherein the monomer is tetrafluoroethylene.

3. The prosthesis or sponge of claim 1 further comprising a supporting material to which said copolymer is applied.

4. The prosthesis or sponge of claim 3 wherein said supporting material is selected from the group consisting of a polymer, ceramic, metal, glass and preformed membrane.

5. The prosthesis or sponge of claim 4 wherein said polymer is a porous polymer.

6. The prosthesis or sponge of claim 5 wherein said porous polymer is polytetrafluoroethylene or expanded polytetrafluoroethylene.

7. The prosthesis or sponge of claim 5 wherein the porous polymer is knitted or woven polyester.

8. The prosthesis or sponge of claim 5 wherein the porous polymer is polyurethane.

9. The prosthesis of sponge of claim 1 in the form of a tube.

10. The prosthesis or sponge of claim 1 wherein the surface further comprises adsorbed adhesive proteins.

11. The prosthesis or sponge of claim 10 wherein said adhesive proteins are derived from serum.

12. The prosthesis or sponge of claim 11 wherein said adhesive serum proteins are selected from the group consisting of fibronectin, vitronectin, thrombospondin and adhesive fragments of any of these proteins.

13. The prosthesis or sponge of claim 1 wherein the surface further comprises animal cells adhered thereto.

14. A surface for the attachment and growth of animal cells in vivo, said surface comprising the neutralized form of a copolymer of perfluoro-3,6-dioxa-4-methyl-7-octene sulphonyl fluoride and monomer with animal cells adhered thereto.

15. A process for the preparation of a surface for the attachment and growth of animal cells in vivo, said process comprising applying a copolymer of perfluoro-3-, 6-dioxa-4-methyl-7-octene sulphonyl fluoride and a monomer to an appropriate substrate, neutralizing the resultant surface and adhering animal cells to the surface.

16. A process for the attachment and growth of animal cells in vivo comprising: exposing animal cells to a prosthesis or sponge having a surface formed from a neutralized copolymer of perfluoro-3,6-dioxa-4-methyl-7-octene sulphonyl fluoride and a monomer.

17. A process for the attachment and growth of animal cells in vitro comprising: exposing animal cells in vitro to a surface formed from a neutralized copolymer of perfluoro-3,6-dioxa-4-methyl-7-octene sulphonyl fluoride and a monomer.

18. The process of claim 17 which further comprises exposing said surface to a medium containing animal cells and adhesive proteins.

* * * * *